United States Patent [19]

Kung et al.

[11] Patent Number: 5,661,039

[45] Date of Patent: Aug. 26, 1997

[54] PERSPIRATION ASSAY FOR BONE RESORPTION

[75] Inventors: Viola T. Kung, Menlo Park; Baltazar Gomez, Jr., Fremont, both of Calif.

[73] Assignee: Metra Biosystems, Inc., Mountain View, Calif.

[21] Appl. No.: 400,097

[22] Filed: Mar. 1, 1995

[51] Int. Cl.$^6$ .................. G01N 33/566; A61K 38/00; C07D 401/00; A61F 7/00

[52] U.S. Cl. .................. 436/501; 530/323; 436/547; 546/276.4; 604/312

[58] Field of Search .................. 604/4–6, 21, 312; 546/281, 261, 291; 436/819, 501, 547; 530/404–406

[56] References Cited

U.S. PATENT DOCUMENTS

| | | | |
|---|---|---|---|
| 4,973,666 | 11/1990 | Eyre | 530/323 |
| 5,140,103 | 8/1992 | Eyre | 530/327 |
| 5,283,197 | 2/1994 | Robins | 436/87 |
| 5,350,855 | 9/1994 | Daniloff et al. | 54/291 |
| 5,502,197 | 3/1996 | Daniloff et al. | 546/281 |
| 5,527,715 | 6/1996 | Kung | 436/547 |

FOREIGN PATENT DOCUMENTS

| | | |
|---|---|---|
| 556152A1 | 8/1993 | European Pat. Off. . |
| WO91/10141 | 7/1991 | WIPO . |
| WO94/03814 | 2/1994 | WIPO . |
| WO94/14072 | 6/1994 | WIPO . |
| 9535504 | 12/1995 | WIPO . |

*Primary Examiner*—John G. Weiss
*Assistant Examiner*—David J. Cho
*Attorney, Agent, or Firm*—Vincent M. Powers; Dehlinger & Associates

[57] ABSTRACT

A method of screening for the presence of a bone resorption abnormality is disclosed. The method includes obtaining a sweat sample from the subject, and determining the level of native free pyridinoline (Pyd) and/or deoxypyridinoline (Dpd) in the sample. The determined level is compared with a predetermined level characteristic of normal subjects, and an above-normal level is an indication that the subject has a bone resorption abnormality.

9 Claims, No Drawings

PERSPIRATION ASSAY FOR BONE RESORPTION

FIELD OF THE INVENTION

The present invention relates to a diagnostic assay based on sweat collection.

REFERENCES

Black, D., et al., *Anal. Biochem.* 169:197–203 (1988).
Campbell, A., *Monoclonal Antibody and Immunosensor Technology*, Elsevier (1991).
Cerelli, M. J., et al., PCT Publication No. WO 94/03814 (App. No. PCT/US93/07203) (1994).
Colwell, A., et al., in *Current Research in Osteoporosis and Bone Mineral Measurement*, Vol. 2, F. Ring, Editor, British Institute of Radiology, London, p. 5 (1992).
Eyre, D. R., et al., *Anal. Biochem.* 137:380–388 (1984).
Harlow, E., et al., *Antibodies: A Laboratory Manual*, Cold Spring Harbor Lab (1988).
James, I., et al., *J. Chromatogr.* 612:41–48 (1993).
James, I., et al., *Clin. Rheumatol.* 10:457 (1991).
Kung, V. et al., PCT Publication No. WO 94/14072 (App. No. PCT/US93/12321) (1994).
Pratt, D. A., et al., *Anal. Biochem.* 207:168–175 (1992).
Robins, S. P., PCT Publication No. WO 91/10141 (App. No. PCT/GB90/02030) (1991).
Segel, I., *Biochemical Calculations*, John Wiley and Sons, (1976).
Seibel, et al., *J. Rheumatol.* 16:964–970 (1989).
Wong, S. S., *Chemistry of Protein Conjugation and Cross-Linking*, CRC Press, Boca Raton, Fla. (1991).

BACKGROUND OF THE INVENTION

There are a variety of conditions in humans which are characterized by a high level of bone resorption and/or by an abnormal balance between bone formation and bone resorption. Among the more common of these are osteoporosis, Paget's disease, and conditions related to the progress of benign and malignant tumors of the bone and metastatic cancers that have migrated to bone cells from elsewhere in the body, e.g., from prostate or breast initial tumors. Other conditions associated with changes in collagen metabolism include osteomalacial diseases, rickets, abnormal growth in children, renal osteodystrophy, and drug-induced osteopenia. Further, abnormalities in bone metabolism are often side effects of thyroid treatment and thyroid conditions per se, such as primary hypothyroidism and thyrotoxicosis as well as Cushing's disease.

It has been recognized that disorders of bone resorption or other conditions characterized by an abnormal balance between bone formation and bone resorption can be detected by altered levels of pyridinium crosslinks in urine and serum (e.g., PCT Pub. Nos. WO 94/14072 (Kung et al.), WO 94/03814 (Cerelli et al.), WO 91/10141 (Robins), WO 91/08478 (Eyre) and WO 89/04491 (Eyre)). The crosslinks take the form of compounds containing a central 3-hydroxy pyridinium ring in which the ring nitrogen is derived from the epsilon amino group of lysine or hydroxylysine, and which occur in collagen as trivalent crosslinking species which crosslink the three polypeptide chains in collagen. In urine and blood, the crosslinks are present as a mixture of pyridinium species consisting of the central pyridinium core (pyridinoline or deoxypyridinoline) with and without additional collagen amino acid residues and/or glycosyl groups still attached.

However, analyses of urine or blood entail certain disadvantages. Assays based on blood generally require samples to be collected by specially trained personnel, increasing the cost of the procedure. Also, blood samples may create the risk of transmitting diseases such as AIDS to those involved with collecting, transporting, and analyzing the samples. Assays based on urine, on the other hand, are often associated with patient discomfort in relation to collecting the sample. In the present invention, these problems are avoided using a method based on collection and analysis of a sweat sample.

SUMMARY OF THE INVENTION

The present invention includes, in one aspect, a method of screening for the presence of a bone resorption abnormality in a human subject. The method includes obtaining a sweat sample from the subject, and determining the level of native free pyridinoline (N-Pyd) and/or native free deoxypyridinoline (N-Dpd) in the sample. The determined level is compared with a predetermined level characteristic of normal subjects, and an above-normal level is an indication that the subject has a bone resorption abnormality. In one embodiment, the sample level is measured by immunoassay using antibodies specific for the selected crosslinks.

The method may also be used to monitor a change in the status of bone resorption in a subject, in response to a therapeutic treatment, by further monitoring the level of Pyd and/or Dpd during or following such treatment.

These and other objects and features of the invention will become more fully apparent in view of the following detailed description of the invention.

DETAILED DESCRIPTION OF THE INVENTION

I. Definitions

As used herein, the terms below have the following definitions:

"Pyd" or "pyridinoline" or "free pyridinoline" refers to the compound shown at I below, where the pyridinium ring nitrogen derives from the ε amino group of a hydroxylysyl residue.

"Dpd" or "deoxypyridinoline" or "free deoxypyridinoline" refers to the compound shown at II below, where the pyridinium ring nitrogen derives from the ε amino group of a lysyl residue.

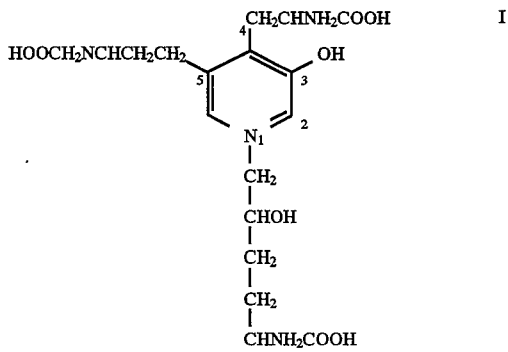

-continued

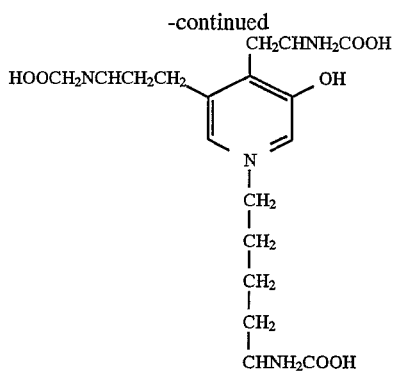

"Free crosslinks" refers to compound I, compound II, or both, i.e., pyridinoline and/or deoxypyridinoline crosslink species free from covalently attached amino acids, peptides, and glycosyl groups.

"Glycosylated pyridinoline" or "glyco-Pyd" refers to glycosylated forms of compound I, wherein glycosyl groups are covalently bound to the aliphatic hydroxyl group. Two exemplary glyco-Pyd compounds are Gal-Pyd and Glc.Gal-Pyd, which contain the acetal groups shown at III and IV below, respectively.

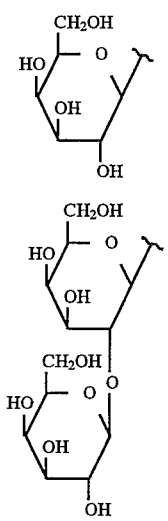

"Pyd-peptides" refers to peptide-derivatized forms of compound I, in which one or more of the three amino acid residues in the compound are linked by peptide linkages to additional amino acid residues. Similarly, "Dpd-peptides" refers to peptide-derivatized forms of compound II, in which one or more of the three amino acid residues in the compound are linked via peptide linkages to additional amino acid residues. "Pyridinium-peptides" refers to a mixture of Pyd-peptides and Dpd-peptides.

"Pyd-peptides having a molecular weight greater than 1000 daltons" or "Pyd-peptides (MW>1000)" refers to Pyd-peptides retained by a dialysis membrane having a 1,000 molecular weight cutoff. Similarly, "Dpd-peptides having a molecular weight greater than 1000 daltons" or "Dpd-peptides (MW>1000)" refers to Dpd-peptides retained by a dialysis membrane having a 1,000 molecular weight cutoff.

"Pyd crosslinks" refers to pyridinium compounds which contain compound I either in free or peptide-derivatized form. Pyd crosslinks include Pyd, glyco-Pyd and Pyd-peptides. Similarly, "Dpd crosslinks" refers to the pyridinium crosslinks which contain compound II either in free or peptide-derivatized form. "Dpd crosslinks" include Dpd and Dpd-peptides.

"Pyridinium crosslinks" refers to pyridinium crosslinks which contain compounds I and/or II in free and/or peptide-linked form.

"Total Pyd" or "T-Pyd" refers to the total quantity of Pyd crosslinks present, as measurable by acid hydrolysis of a sample to completely convert Pyd crosslinks to free Pyd. Similarly, "total Dpd" or "T-Dpd" refers to the total quantity of Dpd crosslinks present.

"Hydrolysed-Pyd" of "H-Pyd" refers to Pyd produced by hydrolyzing Pyd crosslinks in 6N HCl at 110° C. for 16 hours. Similarly, "hydrolysed-Dpd" of "H-Dpd" refers to Dpd produced by hydrolysing Dpd crosslinks in 6N HCl at 110° C. for 16 hours.

As used herein, "mammal" has its standard meaning. Examples of mammals relevant to the present application include humans, dogs, cats, horses, cows, sheep, pigs, rabbits, rats, and mice.

"Bone resorption abnormality" or "bone resorption condition" refers to a condition characterized by an elevated level of bone degradation (resorption) in a mammalian subject. Bone resorption conditions include osteoporosis, osteoarthritis, rheumatoid arthritis, primary hyperparathyroidism, hyperthyroidism, Paget's disease, bone cancers (e.g., metastases in bone), osteomalacia, rickets, renal osteodystrophy, and drug-induced osteopenia.

As used herein, "sweat" and "perspiration" are intended to mean the same thing and are used interchangeably herein.

II. Free Crosslink Detection

In practicing the method of the present invention, the levels of the free pyridinium crosslinks, N-Pyd and/or N-Dpd, are measured by any analytical method capable of quantitatively measuring these compounds without significant interference from other components in sweat. For this purpose, suitable methods may include chromatographic, electrophoretic, and immunoassay methods, or combinations thereof.

Where the free pyridinium crosslinks are measured by non-immunological methods, the crosslinks can be measured by fluorescence detection based on their intrinsic fluorescence properties. N-Pyd and N-Dpd strongly fluoresce with peak emission at 390–400 nm when subjected to an excitation source at about 297 nm (Black et al., 1988; Eyre et al., 1984). Chromatographic (James et al., 1993) and capillary electrophoresis (James et al., 1991) techniques for fluorimetrically measuring Pyd and Dpd have been described. Alternatively, the crosslinks may be measured based on UV-absorbance properties as described by Colwell et al. (1992).

N-Pyd and N-Dpd may also be measured by immunoassay techniques employing antibodies specific for N-Pyd, N-Dpd, or both. The antibodies may be monoclonal or polyclonal, as described further below. With regard to specificity, the antibodies should be sufficiently specific for the selected crosslinks (N-Pyd and/or N-Dpd) to avoid spurious results due to binding other sweat components.

Screening and selection for such antibodies may be based on affinity for N-Pyd or N-Dpd alone, where an antibody showing an affinity for N-Pyd and/or N-Dpd of greater than about $10^7$/molar, preferably greater than about $10^8$/molar, is usually specific enough for the purposes of the invention. Binding affinity can be determined by known methods, e.g., by Scatchard analysis using an ELISA assay (Campbell, Segel). Accordingly, in one embodiment, the antibody reagent used in the invention has a binding affinity constant for the selected free crosslink species of greater than about $1\times10^7$/molar, and preferably greater than about $1\times10^8$/molar.

In addition, the screening process may be based on additional binding criteria, such as low affinities for amino acids, polypeptides, and/or other components of sweat. For this purpose, it is convenient to measure the binding affinities of the antibodies with respect to certain pyridinium peptide forms that are obtainable from urine. Methods for obtaining such pyridinium peptide forms are described in Example 1 below. These peptides, which can be categorized by molecular weight (e.g., >1000 MW), consist of pyridinoline and deoxypyridinoline species that include peptides covalently attached to one or more amino and/or carboxyl groups of the pyridinium moiety. A high affinity for the selected free crosslinks (N-Pyd and/or N-Dpd) in combination with a relatively low affinity for N-Pyd or N-Dpd peptide forms (e.g., a binding affinity ratio of less than about 5:1 for free:peptide forms) is thus one additional criterion that can be used in the screening process. Accordingly, in one general embodiment, the antibodies have a ratio of reactivity toward the selected native free pyridinium crosslink and urinary pyridinium peptides larger than 1,000 daltons in molecular weight, of greater than about 5:1.

As another binding criterion, the antibodies can be tested for cross-reactivity with free amino acids. For this purpose, an amino acid mixture comprising all 20 standard amino acids at selected concentrations can be used, such as the amino acid mixture employed in Example 7 below.

The antibodies for use in the invention may be specific for N-Pyd, N-Dpd, or both, including antibodies which are specific for one and have moderate crossreactivity (e.g., 40%) with the other. In a more specific embodiment, where the antibody is highly specific for N-Pyd, the antibody preferably has a ratio of reactivity toward native free pyridinoline and native free deoxypyridinoline of greater than about 5:1, preferably greater than about 20:1, and more preferably greater than about 100:1. Where the antibody is for binding N-Dpd, the antibody preferably has a ratio of reactivity toward native free deoxypyridinoline and native free pyridinoline of greater than about 5:1, preferably greater than about 25:1, and more preferably greater than about 100:1. Where the antibody is for binding both native free pyridinoline and native free deoxypyridinoline, the antibody preferably has a ratio of reactivity toward native free pyridinoline and native free deoxypyridinoline of between about 2:1 and 1:2. Antibodies in accordance with such properties are disclosed in PCT Pub. Nos. WO 94/14072 (Kung et al.) and WO 94/03814 (Cerelli et al.), which are incorporated herein by reference.

Example 7 illustrates a competitive binding assay for determining the relative specificities of an antibody for N-Pyd, N-Dpd, and other test materials. Briefly, purified N-Pyd, N-Dpd, urinary pyridinium crosslinks >1000 MW, and an amino acid mixture containing the 20 common amino acids in equimolar amounts (150 µM each), are reacted with a limiting amount of a crosslink-specific antibody in the presence of a selected free crosslink (e.g., N-Pyd, when seeking N-Pyd-specific antibodies) immobilized on a solid-support under conditions where the test materials compete with the support-bound crosslink for binding to the antibody. The extent of binding of antibody to the support-immobilized crosslinks provides a measure of the relative reactivities of the test materials for the antibody.

The adequacy of binding specificity for selected antibodies may be verified using a complementary measurement technique (e.g., capillary electrophoresis or C-18 reversed phase HPLC), or by spike-recovery experiments, where known amounts of N-Pyd or N-Dpd are added to sweat samples and the resultant measured levels are compared with predictions based on the level of N-Pyd or N-Dpd measured in the original sample.

The immunogen for producing the antibody reagent is Dpd or Pyd conjugated to a carrier molecule, typically a carrier protein such as keyhole limpet hemocyanin (KLH) or a mammalian serum albumin. The Pyd and Dpd can be native, hydrolyzed, or synthetic. Methods for obtaining N-Pyd and N-Dpd are known (Black et al., 1988; Seibel et al., 1989; Robins, 1991; and Cerelli et al., 1994), with a particular method provided in Example 1. Similarly, hydrolyzed Pyd or Dpd can be produced by acid hydrolysis of pyridinium cross-links in bone collagen or urine, as described in Black et al. (1988) and Seibel et al. (1989).

In another approach, the Pyd and Dpd are prepared synthetically, as described, for example, in EPO Publication No. 556152 A1 (Revesz, 1993).

Coupling of Pyd or Dpd to a carrier protein is by standard coupling methods, typically using a bifunctional coupling agent which forms, at one coupling end, an amide linkage with one of the free carboxyl (or amino) groups of Pyd or Dpd, and at the other coupling end, an amide or ester or disulfide linkage to the carrier protein according to standard methods. Alternatively, in a preferred embodiment, the Pyd or Dpd can be directly coupled to the protein, e.g., in the presence of a water-soluble carboxyl activating agent such as EDC (1-(3-dimethylaminopropyl)-3-ethylcarbodiimide), also according to well known methods. The latter approach is illustrated in Examples 2A and 2B, which describe the coupling of Pyd to bovine serum albumin (BSA) and keyhole limpet hemocyanin (KLH) by EDC activation. General coupling reactions for derivatizing a carrier protein with a peptide antigen are given in Harlow (1988, pp. 77–87) and Wong (1991).

For preparing monoclonal antibodies, an immunogen of the type above is used to immunize an animal, such as a mouse, from which antigen-specific lymphocytes can be obtained for immortalization. One suitable animal is the "autoimmune" MRL/MpJ-lpr mouse available from Jackson Laboratory (Bar Harbor, Minn.).

Where an antibody specific for N-Pyd is desired, a Pyd-immunogen is typically used. Likewise, where an antibody which is specific for N-Dpd is desired, a Dpd-immunogen is typically used. An antibody which recognizes both Pyd and Dpd may be obtained using a Pyd-immunogen or a Dpd-immunogen.

To produce the desired antibodies, the hybridoma cell line is grown in a suitable medium (Harlow, pp. 247–270), such as Dulbecco's modified Eagle's medium (DMEM) supplemented as described in the Materials and Methods section below. Monoclonal antibodies ("Mabs") are harvested from the medium and can be concentrated and stored according to published methods (Harlow pp. 271–318). An examplary protocol for preparing monoclonal antibodies having the desired specificity is provided in Example 3. The properties of monoclonal antibodies specific for N-Pyd, N-Dpd, and both N-Pyd and N-Dpd, are shown in Tables 4–6 in Example 3.

Polyclonal antibody preparation is by conventional techniques, including injection of the immunogen into suitable mammalian subjects, such as rabbits, sheep or mice, according to immunological protocols generally known in the art (e.g., Harlow, pp. 93–115). Typically, rabbits are injected subcutaneously with the immunogen in an adjuvant, and booster immunizations are given by subcutaneous or intramuscular injection every 2–3 weeks; mice may be injected intraperitoneally according to a similar schedule. Blood is collected at intervals, e.g. 1–2 weeks after each immunization injection. Antisera may be titrated to determine antibody formation with respect to N-Pyd or N-Dpd, according to standard immunoprecipitation methods (Harlow, pp. 423–470). Details of one method for producing polyclonal antibodies in rabbits are given in Example 4.

The binding affinity for polyclonal antisera can be determined by known methods and represents an average binding affinity constant for the antibodies in the antisera which are specific against the selected free crosslinks. Polyclonal antibodies obtained from rabbit VI-8 (Example 4) were found to have a binding constant for N-Pyd of about $1\times10^8$, as determined by Scatchard analysis. Other binding properties of the polyclonal antibodies from rabbit VI-8 are shown in Table 9.

For clinical use, crosslink-specific antibodies of the type above may be formulated in a diagnostic kit. The kit includes an antibody of the type described above, and any other suitable reagents for carrying out the assay. The assay format may be heterogeneous or homogeneous.

The immunoassay kit may take the form of a competitive assay, in which a selected amount of free crosslinks is immobilized on a solid support, for competing with free crosslinks from the sample for binding to crosslink-specific antibodies. Conveniently, the assay includes reporter-labeled second antibodies for binding to the crosslink-specific antibodies, allowing the amount of crosslink-specific antibody bound to the solid support to be determined. The label can be a radioisotope, a fluorescent or chemiluminescent label, or an enzyme, for example. Reporter-labeled second antibodies are commercially available or are readily constructed (Harlow, pp. 319–358) for a variety of reporter moieties. One preferred reporter is alkaline phosphatase, which can react with a p-nitrophenylphosphate substrate to produce a colored product having a strong absorption peak at 405 nm. An exemplary immunoassay protocol is provided in Example 6 below.

The reporter-labeled second antibody is typically an anti-IgG antibody, such as an anti-rabbit-IgG antibody, where the crosslink-specific antibodies are polyclonal antibodies obtained from immunized rabbits, or an anti-mouse-IgG antibody, where the crosslink-specific antibodies are mouse monoclonal antibodies. It will be appreciated that various other detection modes may be employed, such as a biotin-labeled second antibody in combination with a reporter-labeled streptavidin.

Alternatively, the crosslink-specific antibody itself can be labeled with a reporter.

In another competitive format, the crosslink-specific antibodies are immobilized on a solid support, and cross-links from the sample compete with reporter-labeled free crosslinks for binding to the immobilized antibody. The antibodies may be attached to the solid support by a variety of known methods, including chemical derivatization or high-affinity binding of the antibody by support-bound protein A or anti-IgG antibody, according to standard methods. Reporter-labeled free crosslinks can be prepared by standard methods as well, by covalent attachment of the selected label to the amino or carboxyl groups present in the free crosslinks, for example. A detailed example of this type of assay format for measuring N-Pyd or N-Dpd is described in PCT Publication No. 94/14072 (Kung et al.).

It will be appreciated that a number of other immunoassay techniques may be used, such as radioimmunoassays, coupled enzyme assays, fluorescence-based assays, chemiluminescence assays, and EMIT-type assays.

III. Assay Method

As noted above, the invention includes a method of screening for the presence of a bone resorption abnormality in a mammalian subject, particularly a human subject. In the method, a sweat sample is obtained from the subject, and the level of selected pyridinium Pyd, N-Dpd, that is, of N-Pyd, N-Dpd, or a combination thereof, is determined in the sample. The measured level is compared with the level characteristic of normal subjects, and an above-normal level is an indication that the subject has a bone resorption abnormality.

The sweat sample is collected by any suitable means known in the art for sweat collection. In one embodiment, the sample is collected in liquid form directly from a subject's skin, after the subject has undergone moderate exercise (e.g., a repetitive stationary exercise or running on a treadmill) sufficient to generate beads of perspiration. The sample is collected from any convenient site, such as the forehead, underarm area, or abdomen, for example, in an amount sufficient to allow measurement of the pyridinium crosslink species of interest (e.g., 20–200 µl). Conveniently, a pipette is used to obtain the sample. Alternatively, the sweat liquid may be collected by dabbing perspiration-laden skin with an absorbent pad or sponge which is then compressed or centrifuged to release the collected liquid, or alternatively, washed to remove the collected liquid from the pad for later assay. The sample may then be stored in a vial, or in dry form in a pad or on a solid surface for later resuspension and analysis.

In another embodiment, the sample is collected in a pad (or patch), which is contacted with dry skin for a selected period of time, to continuously collect perspiration from the subject. The pad may be single- or multi-layered. Preferably, at least one of the layers is composed of an absorbent material which is substantially unreactive towards free pyridinium crosslinks, and from which such crosslinks can be easily separated using water or organic solvent. Suitable absorbent materials include cotton, cellulose fiber, non-woven rayon, although any material satisfying the above criteria may be used.

The pad may be coated with a liquid-impervious layer which prevents evaporation of the collected sweat from the pad. Alternatively, the pad is constructed without a liquid-impervious layer, so that perspiration is continuously collected and evaporated, leading advantageously to concentration of sweat constituents in the pad. Methods of preparing various pads for collecting sweat are discussed, for example, in U.S. Pat. No. 4,756,317 issued Jul. 12, 1988 to Eckenhoff et al.; U.S. Pat. No. 5,036,861 issued Aug. 6, 1991 to Sembrowich et al.; U.S. Pat. No. 5,050,604 issued Sep. 24, 1991 to Reshef et al.; U.S. Pat. No. 5,076,273 issued Dec. 31, 1991 to Schoendorfer et al.; and PCT Pub. No. WO 94/14062 (Schoendorfer), which are all incorporated herein by reference.

It will be appreciated that the size and composition of the pad will affect the rate and/or quantity of sample collected in a given time period. With a larger pad, for example, a shorter collection time can be used to collect an adequate sample. Similarly, a pad designed to allow rapid evaporation of sweat will enhance the amount of sample collected relative to a pad that prevents evaporation. In terms of surface area, a range of sizes may be used, typically covering an area of between 0.1 and 10 $cm^2$, although pads having other sizes may be used.

In yet another embodiment, the sweat sample is collected by suction, using an air-tight housing placed over a selected area of the skin and which draws liquid sweat into a flow cell for analysis (e.g., as described in EP Publication No. 513, 789 A1), or into a collection trap or filter where the sweat evaporates, leaving the non-volatile constituents on the filter for later analysis.

After the sample has been collected, the sample is stored, if necessary, and subsequently analyzed to determine the level of N-Pyd and/or N-Dpd by methods discussed above. Prior to the analysis, the sample may be centrifuged or filtered to remove particulate matter if necessary.

In practicing the present invention, it is necessary to ascertain an average level or range of the selected free crosslinks which is characteristic of normal subjects for the particular mode of sample collection selected, to provide a standard against which levels measured in test subjects may be compared. Thus, free crosslink levels will ordinarily be measured in sweat samples from control subjects who are in good health. The makeup of the control group may be tailored according to the characteristics of the population to be tested. For example, the control group may be limited to a particular age group, e.g. 25–55 year old males, or 25–44 year old premenopausal females, to obtain baseline levels. Other parameters of interest may include the subjects' weight, race, or gender for example. The determined average or range of free crosslinks in the normal subjects is then used as a benchmark for detecting above-normal levels indicative of a bone resorption abnormality.

In embodiments where significant evaporation has occurred during sample collection, it may be desirable to measure an additional component of sweat as an internal standard, to control for dilution or concentration of the sample during or following collection. One suitable component in sweat is creatinine, whose concentration may be measured by methods well known in the diagnostic arts. Since the level of creatinine is ordinarily independent of bone resorption, the measured creatinine level provides an internal standard relative to which the concentration of N-Pyd and/or N-Pyd can be assessed. An elevated ratio of N-Pyd/creatinine or N-Pyd/creatinine, relative to the ratio characteristic of normal subjects, is an indication of the presence of a bone resorption abnormality.

Conversely, when sweat samples are collected as drops of sweat by pipetting or otherwise, so that no evaporation is allowed to occur, the use of creatinine or other internal standard may be avoided since the concentration of crosslinks in the sample has not been altered.

IV. Utility

The present invention provides a method of screening for bone resorption abnormalities which avoids disadvantages associated with the testing of blood or urine.

The method may also be used in veterinary applications for detecting and monitoring bone resorption abnormalities that occur among farm animals and house pets. Conditions that produce destruction of alveolar bone are common among cats, horses and dogs, and often require veterinary treatment. The method may also be used with other diagnostic methods, such as radiographic techniques and assays directed to other indicators of bone resorption status, to provide a fuller picture of the subject's status.

From the foregoing, it will be appreciated how various objects and features of the invention are met. The invention provides simple, non-invasive methods of screening for and monitoring bone resorption conditions. The method may also allow the monitoring of changes in disease status during or following therapeutic treatments. Furthermore, being based on measurements in a subject's sweat, the method avoids disadvantages associated with blood and urine samples.

The following examples are intended to illustrate, but in no way limit the invention.

EXAMPLES

Materials and Methods

Female autoimmune MRL/MpJ-lpr mice were purchased from the Jackson Laboratory, Bar Harbor, Me.

Mouse non-secreting P3X63Ag8.653 myeloma cells, and mouse monocyte-macrophage cell lines P388D1 (IL-1) and J774A.1 were purchased from American Type Culture Collection (ATCC), Rockville, Md.

Adjuvant Ribi and Ribi(CWS) were purchased from RIBI Immunochem Research, Inc., Hamilton, Mont. 50% PEG 1500 (polyethylene glycol 1500, 50% w:v in water) was purchased from Boehringer Mannheim, Indianapolis, Ind. HAT and HT were purchased from Sigma Chemical Company, St. Louis, Mo.

Dulbecco's Modified Eagle Medium (DMEM), NCTC-109, and gentamicin were purchased from Gibco, Grand Island, N.Y. Fetal clone bovine serum was from Hyclone Laboratories, Inc., Logan, Utah. Oxaloacetic acid and insulin were from Sigma Chemical Company. S-DMEM was formulated as follows, where the percentages indicate final volume percentages in the final medium: DMEM (80%), NCTC-109 (10%), fetal clone bovine serum (10%), oxaloacetic acid (1 mM), L-glutamine (2 mM), gentamicin (50 µg/ml) and insulin (10 µg/ml).

For preparation of conditioned media, mouse monocyte cell lines P388D1 (IL-1), or interchangeably, cell line J774A.1, were grown in S-DMEM medium, with a 1:4 split twice a week. Every 3 days, tissue culture supernatants were filtered through a 0.2 micron filter and then supplemented with 4 mM L-glutamine. The resultant concentrated conditioned media were used as 20% supplement for S-DMEM to raise hybridoma cells.

Unless stated otherwise, PBS is defined as a buffer containing 0.01M phosphate and 150 mM NaCl, pH 7.

EXAMPLE 1

Purification of Crosslinks

For preparing N-Pyd, N-Dpd, and pyridinium peptide crosslinks having a molecular weight greater than 1000 daltons, human urine was filtered through a 3000 dalton molecular cut-off filter (Filton Co.) using 40 psi of back pressure. The filtrate was then lyophilized and reconstituted in ⅟20 of the original volume with 0.2M acetic acid.

The concentrated urine was then applied to a Sephadex G-10 (2.6×95 cm) column equilibrated with 0.2M acetic acid. Fractions eluted from the column were analyzed for free Pyd and free Dpd by HPLC (Black et al., 1988). The free crosslink-containing fractions were pooled together, adjusted to pH 2.0 and applied onto 1×18 cm cation exchange column (Lacarte Co., UK) and equilibrated with 0.1M sodium citrate pH 4.2.

Glyco-Pyd, Pyd and Dpd were coeluted thereafter from the ion exchange column with 0.1M sodium citrate pH 4.2. Collected fractions were analyzed for the presence of crosslinks by HPLC analysis as above. Fractions containing N-Pyd and N-Dpd were pooled together and applied to 2.5×10 cm reverse phase C-18 column (Waters) which was subsequently developed with 2–20% gradient of acetonitrile containing 0.1% HFBA. Separated fractions (glyco-Pyd, Pyd and Dpd) were collected and concentrated by lyophilization. The dry residue was reconstituted in 0.2M acetic acid and stored at 4° C.

Urinary pyridinium-peptides (MW<1000 MW) were prepared by exhaustive dialysis of human urine using 1000 dalton molecular weight cut-off dialysis membranes (Spectra-Por). The T-Pyd and T-Dpd crosslink contents of the pyridinium peptides were determined by hydrolyzing peptide samples with 6N HCl at 110° C. for 16 hours followed by HPLC analysis for Pyd and Dpd.

Preparative amounts of H-Pyd and H-Dpd were obtained from hydrolyzed powdered bovine or sheep bone as described by Black et al. (1988).

EXAMPLE 2

Immunogen Preparation

A. Pyd-BSA Immunogen

To a 3.1 ml solution consisting of 9 mg of bovine serum albumin (BSA) and 3.8 mg of Pyd in 0.1M MES pH 5.0 was added an 0.88 ml aqueous solution containing 88 mg of EDC. The mixture reacted for four hours at room temperature then was exhaustively dialysed versus phosphate buffered saline pH 7.0 (PBS). UV and fluorescence measurements indicated 5.8 moles of pyridinoline substituted per mole of albumin.

B. Pyd-KLH Immunogen

To a solution of dried H-Pyd (6 mg) in water adjusted to pH 5±0.5 (200 µl) was added 2 ml of a 10 mg/ml solution of keyhole limpet hemocyanin (KLH) in PBS. To the mixture was added 30 mg solid 1-(3-dimethylaminopropyl)-3-ethylcarbodiimide (EDC, Pierce), and ten minutes later, another 30 mg of EDC, and the reaction was allowed to proceed for 4 h at room temperature. The reaction mixture was then exhaustively dialyzed versus PBS, after which the Pyd-KLH immunogen was collected and stored.

EXAMPLE 3

Preparation of Anti-Pyd Monoclonal Antibodies

A. Immunization Protocol

Female 5-week-old autoimmune MRL/MpJ-lpr mice immunized using the protocol below:

TABLE 3

Immunization Protocol for Pyd Mice

| Immuniz-ation | Days from Fusion | Immunogen Injected (µg) | [1]Adjuvant | Inject. Made |
|---|---|---|---|---|
| 1 | 60 | 100 | Ribi | ip[2] |
| 2 | 46 | 100 | Ribi | ip |
| 3 | 32 | 100 | Ribi | ip |
| 4 | 18 | 100 | Ribi | ip |
| 5 | 4 | 200 | — | iv[3] |

[1]Adjuvant and antigen were suspended in Hank's balanced salt solution
[2]Intraperitoneal
[3]Intravenous On the day of fusion, the immunized mouse was sacrificed by $CO_2$ gas, and the spleen was excised from the mouse and placed in a culture dish containing 5 ml of serum-free DMEM medium preheated to 37° C. Following removal of adipose tissue attached to the spleen, the spleen was washed with 5 ml of serum-free DMEM medium. The spleen was then cut into small pieces which were placed in a cell homogenizer containing 7 ml of serum-free DMEM medium, and the cells were homogenized to form a cell suspension.

B. Fusion Protocol

The following steps were performed at room temperature.

The spleen cell suspension (~2×10⁸ cells in serum-free DMEM medium) and log-phase P3X63Ag8.653 myeloma cells (~7×10⁷ cells in serum-free DMEM medium) were centrifuged independently at 400×g for 10 min. The resultant cell pellets were suspended together in serum-free DMEM medium (10 ml) in a 50 mL centrifuge tube and then centrifuged at 400×g for 10 min. The supernatant was removed completely, and the centrifuge tube was tapped to loosen the cell pellet.

For cell fusion, a solution of 50% PEG 1500 (4 ml) was added dropwise to the tube with gentle mixing by pipette over a 90 second period. Next, serum-free DMEM (4 ml) was added dropwise over 1 min. S-DMEM (40 ml) was then added over 2 min with gentle mixing, after which the mixture was mixed by pipette for an additional 2.5 min. The resultant mixture was centrifuged at 400×g for 10 min. After thorough removal of the supernatant, the cells were suspended in 320 ml of HAT in 20% P388D1-conditioned S-DMEM medium. The cell suspension was plated in 16 96-well tissue culture plates, 200 µl/well, and the plates were then incubated at 37° C. in an atmosphere containing 7% $CO_2$. The cell mixtures were fed at day 3 and day 7 by removing 100 µl/well of old medium and adding 150 µl/well of either HAT medium (day 3) or HT medium (day 7). The wells were ready to screen 7 to 10 days after fusion.

C. Screening Hybridomas for Production of Anti-N-Pyd Antibodies

Successful fusion products were screened for immunoreactivity using the immunoassay format described in Example 6. Cell lines which showed high affinity binding to N-Pyd were subcloned by limiting dilution and further screened for production of antibodies with high binding affinity for N-Pyd.

D. Monoclonal Antibodies Specific for N-Pyd and/or N-Dpd

The binding properties of three highly specific antibodies obtained by the procedures outlined in sections A–C above are shown in Tables 4–6. The Pyd-specific antibody shown in Table 4 (from a cell line designated as Pyd XXV-3G6-3B11-1A10) was obtained using H-Pyd-KLH immunogen prepared as in Example 2B. The Dpd-specific and Dpd/Pyd-specific antibodies shown in Tables 5 and 6, respectively (from cell lines designated as Mab-Dpd-II-7B6-1F4-1H11 and Pyd/Dpd-V-6H2-2H4-1E4), were obtained using H-Dpd-KLH, also prepared as in Example 2B.

TABLE 4

| Cross-Reactivity of N-Pyd-Specific Mab | |
|---|---|
| N-Pyd | 100% |
| N-Dpd | 16% |
| Pyd-Peptide (>1000) | <1% |
| Amino Acid Mixture (150 µM) | <1% |

TABLE 5

| Cross-Reactivity of N-Dpd-Specific Mab | |
|---|---|
| N-Dpd | 100% |
| N-Pyd | <1% |
| Dpd-Peptide (>1000) | 13% |
| Amino Acid Mixture (150 µM) | <1% |

TABLE 4

| Cross-Reactivity of Pyd/Dpd-Specific Mab | |
|---|---|
| N-Dpd | 100% |
| N-Pyd | 102% |
| Dpd-Peptide (>1000) | 1% |
| Pyd-Peptide (>1000) | 11% |
| Amino Acid Mixture (150 µM) | 5% |

EXAMPLE 4

Preparation of Anti-Pyd Polyclonal Antibodies

New Zealand white rabbits (a total of 59) for immunization were divided into eight groups according to immunization protocol, as indicated below in Table 7. The immunization dose was 200 µg of Pyd-BSA (Example 2A), low-hapten Pyd-BSA immunogen (prepared as in Example 2A, but with a lower Pyd:BSA stoichiometry), or Pyd-KLH (Example 2B), in 1.0 ml PBS mixed with 1.0 ml of Ribi adjuvant (Ribi Immuno-Chemical Research, Inc.). Initial immunization was by subcutaneous injections at multiple sites, and subsequent booster immunizations were given at three week intervals intramuscularly. Antiserum was collected 10 days after each immunization.

TABLE 7

| Program # | # of Rabbits | # Rabbits Kept | Carrier |
|---|---|---|---|
| I | 4 | 1 | BSA |
| II | 10 | 0 | BSA |
| III | 10 | 2 | BSA |
| IV | 5 | 1 | BSA |
| V | 5 | 2 | BSA |
| VI | 10 | 1 | KLH |
| VII | 5 | 0 | Low Hapten BSA |
| VIII | 10 | 1 | BSA |
| TOTALS | 59 | 8 | |

Upon collection, each antiserum was tested for Pyd binding affinity using the assay format described in Example 6. In brief, binding of anti-Pyd antibodies to Pyd immobilized on a solid support was detected using an alkaline phosphatase-labeled goat anti-rabbit IgG antibody reagent.

Immunized animals were kept if their antisera satisfied the following cross-reactivity criteria: amino acids (AA)<20%; Pyd-peptide<10%; titer>5000; and a 0 to 25 nM Pyd signal separation of>10% of total modulated signal.

Profiles of the most strongly reactive antisera are shown in Table 8 below, as measured using the assay format described in Example 6. The first column indicates the immunization program from which the rabbit antiserum came. The second column indicates the bleeds used for analysis, where the bleeds were characterized separately, and their measured properties averaged to provide the values shown in the table for the respective antisera. The column marked "titer" indicates the average dilution of each antiserum necessary to achieve an optical density reading of 1.2 to 1.6 with a Pyd-negative sample (no Pyd present) in the immunoassay. The column marked "AA" shows the cross-reactivity of each antiserum with the amino acid mixture described in Example 6. The column marked "Pyd-pep>1000 MW" shows the cross-reactivity of each antiserum with Pyd-peptides (>1000 MW). The last column shows the separation between signals for 0 and 25 nM Pyd samples as a fraction of the total modulated signal.

TABLE 8

| Rabbit # | Bleeds | Titer | AA | Pyd-pep. >1000 MW | Sens. 25 nM |
|---|---|---|---|---|---|
| I-3 | 21–28 | 200 K[1] | 2% | 4.6% | 18% |
| III-3 | 11–18 | 20 K | 16% | 8.3% | 37% |
| III-5 | 11–18 | 52 K | 1% | 8.1% | 13% |
| IV-4 | 4–14 | 84 K | 4% | 4.9% | 10% |
| V-3 | 4–14 | 22 K | 18% | 4.0% | 15% |
| V-4 | 11–14 | 9700 | 15% | 5.2% | 29% |
| VI-8 | 2–11 | 30 K | 10% | 0.6% | 61% |
| VIII-4 | 3–10 | 34 K | ~0% | 3.4% | 11% |

[1]K = × 1000.

As can be seen, rabbits III-3, V-4, and VI-8 showed significant modulation of signal from 0 to 25nM N-Pyd. The binding properties of the antibodies with the highest binding activity (VI-8) are shown in Table 9.

TABLE 9

| Cross Reactivity of N-Pyd Polyclonal Antibody | |
|---|---|
| N-Pyd | 100% |
| N-Dpd | <10% |
| Pyd-Peptide (MW > 1000) | <5% |
| Amino Acid Mixture | ~12% |

EXAMPLE 5

Preparation of Pyridinoline-Coated Microplates

Biotin-labeled porcine albumin and a streptavidin-Pyd conjugate were utilized in the microplate coating. Biotinylation of the porcine albumin was carried out by adding 10 mg of biotin-X-2,4-dinitrophenol-X-L-lysine, succinimidyl ester (Molecular Probes) in 400 microliters of dimethylformamide to a 15 ml solution of PBS containing 150 mg of albumin. The mixture was allowed to react for two hours at room temperature, followed by G-25 column chromatography. Spectrophotometric analysis indicated four biotin molecules bound per mole of albumin.

Conjugation of N-Pyd (or H-Pyd) to streptavidin was accomplished by coupling a thiolated streptavidin to Pyd via the coupling agent, SMCC. Thiolated streptavidin was prepared by reaction with N-succinimidyl-3-(2-pyridylthio) proprionate (SPDP, Pierce) as follows. To a 0.75 ml solution of 5 mg of streptavidin in PBS was added 21 uL of dimethylformamide containing 260 ug of SPDP. The mixture was allowed to react for one hour at room temperature, and then was dialysed against PBS. The SPDP-labeled streptavidin was reduced by the addition of dithiothreitol to a final concentration of 10 mM. After incubation for one hour at room temperature, the thiolated streptavidin was purified on a G-25 column.

To form H-Pyd-streptavidin, a solution containing 180 ug of succinimidyl 4-(N-maleimidomethyl)cyclohexane-1-carboxylate (SMCC, Pierce) in dimethylformamide (4 ul) was added to a solution containing 0.5 mg thiolated streptavidin and 50 ug of H-Pyd in 100 µl of PBS. The mixture was allowed to react for 3 hours at room temperature and then was dialysed versus PBS. Spectrophotometric analysis of the resultant Pyd-streptavidin indicated between 1 and 2 equivalents of Pyd bound per equivalent of streptavidin.

Each of the wells in a 96-well ELISA plate were coated with N-Pyd as follows. To each well was added 150 microliters of biotin-albumin solution at 3.8 ug/ml in PBS, followed by an overnight incubation at 2°–8° C. The microplates were washed with PBS containing 0.3% "TWEEN"-20 and blocked by adding 200 ul of albumin at 1 mg/ml with an overnight incubation at room temperature. The microplates were then twice washed with PBS containing 0.05% "TWEEN"-20. The streptavidin-Pyd conjugate is immobilized via the streptavidin mediated binding to biotin. 150 ul of a solution containing streptavidin-Pyd at 100 ng/ml in PBS was added to each well of the biotin-albumin coated microplate. After a one hour incubation at room temperature, the plates are twice washed with PBS containing 0.05% "TWEEN"-20, and then incubated with 200 µL/well of 10% sucrose in 100 mMPBS for 2 hours to improve the stability of the support. After aspiration of the wells, residual liquid was then removed from the microplate by drying overnight in a convection oven at 37° C.

EXAMPLE 6

Immunoassay of Sweat Sample

The following immunoassay was performed using the rabbit polyclonal antibodies characterized in Table 9 above (rabbit VI-8), and the N-Pyd coated microtiter plate described in Example 5.

N-Pyd standard solutions and a sweat sample were tested in duplicate. The standard solutions consisted of 0 nM, 0.6 nM, 1.25 nM, 2.5 nM, 5.0 nM, 10 nM, and 20 nM N-Pyd in assay buffer (0.05% $NaN_3$ in 10 mM sodium phosphate containing 150 mM NaCl, pH 7). The sweat sample (200 µl) for this example was obtained from a healthy subject after moderate exercise. Prior to assay, the sample was spun at 10,000 rpm for 2 minutes in a microfuge to remove particulate materials. The supernatant was collected, and 100 µl was spin-filtered through a Millipore-CD membrane at 10,000 rpm for 5 minutes. (The latter step had no effect on the outcome of the assay.)

Ten microliter aliquots each of standard solution or sweat sample were added to the wells of a N-Pyd coated plate, followed by 65 µl of PBS per well, and 75 µl/well of VI-8 antiserum diluted 7,500-fold in assay buffer (containing 100 mM sodium phosphate, pH 7, 150 mM NaCl, 0.05% "TWEEN"-20, and 0.05% sodium azide). The plate was then incubated at 4° C. overnight. After the wells were washed 3 times with PBS containing 0.05% "TWEEN"-20 (wash buffer), goat anti-rabbit IgG-alkaline phosphatase conjugate (150 µl/well, 1:1000 dilution in assay buffer) was added, and the plate was incubated at room temperature for 1 h. The wells were then washed 3 times with wash buffer.

To each well was added 150 uL of enzyme substrate solution (2 mg/mL of p-nitrophenylphosphate (Sigma) in 1.0M diethanolamine, pH 9.8, containing 1 mM $MgCl_2$). Following a 1 hour incubation at room temperature, 50 µl of 3.0N NaOH was added to each well to stop the enzymatic reaction. The optical density at 405 nm was then measured with a Vmax reader (Molecular Devices Corp.).

The optical density readings (405 nm) from duplicate samples were averaged, and the averaged readings from the N-Pyd standards were used to construct a standard curve of OD reading vs. N-Pyd concentration. From this curve, the free N-Pyd crosslink concentration in each sample aliquot was determined. The measured N-Pyd concentration was 3 nM. The creatinine concentration, measured by the Jaffe method, was 0.19 mM. Thus, the ratio of N-Pyd/creatinine was 15.8 nM/mM.

EXAMPLE 7

Binding Selectively of Antibodies

N-Pyd, N-Dpd, and pyridinium-peptides (MW>1000) were isolated from urine as described in Example 1. Aliquots of the various pyridinium crosslink preparations were hydrolysed to convert the crosslinks in the fractions to H-Pyd and H-Dpd. The concentrations of Pyd in the N-Pyd and H-Pyd preparations, of Dpd in the N-Dpd and H-Dpd preparations, and of Pyd and Dpd in the pyridinium-peptide preparation, were determined by HPLC (Black et al., 1988). In addition, an amino acid solution containing an equimolar mixture of the 20 common amino acids, 150 µM each in PBS, was prepared.

Aliquots (50 µl) of the native crosslink preparations and the amino acid mixture were added in duplicate to Pyd-coated microtitre wells, and each well was assayed for pyridinoline as in Example 6. The optical density readings (405 nm) from duplicate samples were averaged, and from these values, the apparent N-Pyd concentration of each sample was determined using a standard curve established with purified N-Pyd. The percent reactivity of each sample was calculated as a ratio of apparent concentration (measured using the N-Pyd standard curve above) to total Pyd crosslink concentration in the sample determined by HPLC for total H-Pyd (times 100). The relative reactivity determined for purified N-Pyd was arbitrarily set at 100%, and the reactivities of the other crosslink preparations (and the amino acid mixture) were expressed as a percentage of 100.

Although the invention has been described with respect to specific embodiments and examples, it will be appreciated that various changes and modifications may be made without departing from the invention.

It is claimed:

1. A method of screening for or monitoring the level of bone resorption in a mammalian subject, comprising:

obtaining a sweat sample from a mammalian subject, and determining a level of pyridinium crosslinks selected from the group consisting of native non-glycosylated, peptide-free pyridinoline, native peptide-free deoxypyridinoline, or both, in the sample wherein a determined level which is above that characteristic of normal subjects is an indication that the subject has a bone resorption abnormality.

2. The method of claim 1, wherein the bone resorption condition detected is osteoporosis.

3. The method of claim 1, wherein the selected crosslinks are native non-glycosylated, peptide-free pyridinoline.

4. The method of claim 1, wherein the selected crosslinks are native peptide-free deoxypyridinoline.

5. The method of claim 1, wherein the selected crosslinks are native peptide-free pyridinoline and native peptide-free deoxypyridinoline.

6. The method of claim 1, wherein said sample level is measured by immunoassay using antibodies specific for the selected crosslinks.

7. The method of claim 6, wherein said antibodies are monoclonal antibodies.

8. The method of claim 6, wherein said antibodies are polyclonal antibodies.

9. The method of claim 1, for use in monitoring a change in the status of a bone resorption condition in the subject, in response to a therapeutic treatment, which further includes measuring the level of said pyridinium crosslinks in a sweat sample from the subject during or after such treatment.

* * * * *

UNITED STATES PATENT AND TRADEMARK OFFICE
CERTIFICATE OF CORRECTION

PATENT NO. : 5,661,039
DATED : August 26, 1997
INVENTOR(S) : Viola T. Kung and Baltazar Gomez, Jr.

It is certified that error appears in the above-identified patent and that said Letters Patent is hereby corrected as shown below:

Column 4,
Lines 9 and 11, "of" should be -- or --.

Column 7,
Line 12, "Table 9" should be -- Table 7 --;
Line 60, insert -- WO -- in front of "94".

Column 8,
Line 3, "Pyd. N-Dpd" should be -- crosslinks --.

Column 9,
Line 31, after "and/or", "N-Pyd" should be -- N-Dpd --.
Line 32, after "or", "N-Pyd/creatinine" should be -- N-Dpd/creatinine --.

Column 10,
Line 13, delete "clone";
Line 18, delete "clone";
Line 39, after "molecular" insert -- weight -- and change "Filton Co." to
-- Filtron Co. --;
Line 47, after "onto" insert -- a --;
Line 54, after "applied to" insert -- a --;
Line 56, after "with" insert -- a --.

Column 11,
Line 10, after "mg of", "Pyd" should be -- H-Pyd --;
Line 11, delete "an";
Line 36, "Table 3" should be -- Table 1 --.

Column 12,
Line 28, "Tables 4-6" should be -- Tables 2-4 --;
Line 29, "Table 4" should be -- Table 2 --;
Line 32, "Tables 5 and 6" should be -- Tables 3 and 4 --;
Line 37, "Table 4" should be -- Table 2 --;
Line 45, "Table 5" should be -- Table 3 --.

Column 13,
Lines 1 and 12, "Table 7" should be -- Table 5 --;
Lines 35 and 53, "Table 8" should be -- Table 6 --;

UNITED STATES PATENT AND TRADEMARK OFFICE
CERTIFICATE OF CORRECTION

PATENT NO. : 5,661,039
DATED : August 26, 1997
INVENTOR(S) : Viola T. Kung and Baltazar Gomez, Jr.

It is certified that error appears in the above-identified patent and that said Letters Patent is hereby corrected as shown below:

Column 14,
Lines 2 and 4, "Table 9" should be -- Table 7 --.

Column 15,
Line 5, "Table 9" should be -- Table 7 --.

Signed and Sealed this

Third Day of December, 2002

JAMES E. ROGAN
*Director of the United States Patent and Trademark Office*